United States Patent [19]

Inoue et al.

[11] 3,963,716

[45] June 15, 1976

[54] NOVEL 1-PHTHALAZONE DERIVATIVE, A PROCESS FOR ITS PREPARATION AND A PHARMACEUTICAL COMPOSITION CONTAINING IT

[76] Inventors: Michiro Inoue, 6-26-3, Kokuryo, Chofu, Tokyo; Masayuki Ishikawa, 3-14-13, Akatsustrumi, Setagaya, Tokyo; Takashi Tsuchiya, 5-17-25, Minamikoiwa, Edogawa, Tokyo; Takio Shimamoto, 13, Kitamachi, Shinjuku, Tokyo, all of Japan

[22] Filed: Sept. 10, 1974

[21] Appl. No.: 504,745

[30] Foreign Application Priority Data
Oct. 30, 1973 Japan.............................. 48-121260
Oct. 31, 1973 Japan.............................. 48-121757

[52] U.S. Cl. ........................... 260/250 P; 260/335; 260/343.3 R; 424/250
[51] Int. Cl.² ................ C07D 237/32; C07D 491/04
[58] Field of Search................................ 260/250 P

[56] References Cited
UNITED STATES PATENTS
3,864,343  2/1975  Inoue et al. .................... 260/250 P
3,870,792  3/1975  Inoue et al. .................... 260/250 P Primary Examiner—Alton D. Rollins
Assistant Examiner—Mary Vaughn
Attorney, Agent, or Firm—Sherman & Shalloway

[57] ABSTRACT

A pharmaceutically active phthalzone derivative of the following formula

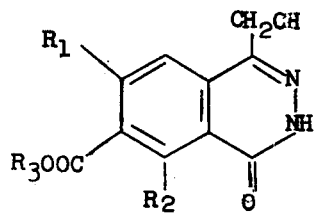

wherein each of $R_1$ and $R_2$ is a member selected from the group consiting of alkyl of from 1 to 3 carbon atoms; $R_3$ is a member selected from the group consiting of alkyl of from 1 to 5 carbon atoms with the proviso that $R_3$ can form together with $R_2$ a member selected from the group consiting of methylene, methyl-substituted and ethyl-substituted methylene. This compound is effectie for treating hypertension, thrombosis and athroscllerosis. A process for its preparation and a pharmaceutical composition containing it are also provided.

3 Claims, No Drawings

NOVEL 1-PHTHALAZONE DERIVATIVE, A PROCESS FOR ITS PREPARATION AND A PHARMACEUTICAL COMPOSITION CONTAINING IT

The present invention relates to a new 1-phthalazone derivative, to a process for its preparation and to a pharmaceutical compositions containing it.

More particularly the invention provides pharmaceutically valuable 1-phthalazone derivative represented by the following formula (I):

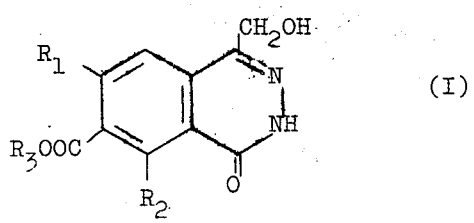

wherein each of $R_1$ and $R_2$ is a member selected from the group consisting of alkyl containing from 1 to 3 carbon atoms; $R_3$ is a member selected from the group consisting of alkyl containing from 1 to 5 carbon atoms, with the proviso that $R_3$ can form together with $R_2$ a member selected from the group consisting of methylene, methyl-substituted and ethyl-substituted methylene.

In the above formula (I), $R_1$ and $R_2$ are each methyl, ethyl, n- and iso-propyl; $R_3$ is methyl, ethyl, n- and iso-propyl, n-, iso-, sec- and tert-butyl, and n-, iso- and sec-amyl with the proviso that $R_3$ can join with $R_2$ to form methylene, methyl-substituted and ethyl-substituted methylene.

The invention also provides a process for preparing a 1-phthalazone derivative of general formula (I), which comprises (a) reacting a compound of the following formula (II):

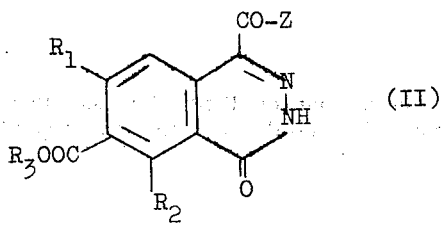

wherein $R_1$, $R_2$ and $R_3$ are as defined above, and Z is a member selected from the group consisting of alkoxy(-preferably $C_{1-3}$ alkoxy), halogen (preferably chlorine and bromine), and a group represented by the formula:

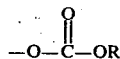

wherein R is methyl or ethyl; with an alkali metal borohydride in the presence or absence of a metal halide, or (b) reacting a compound of the following formula (III):

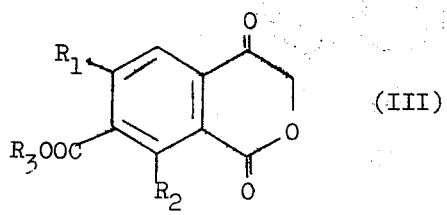

wherein $R_1$, $R_2$ and $R_3$ are as defined above; with hydrazine.

In the specification of U.S. Pat. No. 3,840,662, it has been disclosed that 4-hydroxymethyl-1-phthalazone has pharmaceutical effects on the treatment of hermorrhage, thrombosis and atherosclerosis. Subsequently, U.S. Pat. No. 3,864,343 has disclosed that alkoxycarbonyl-4-hydroxymethyl-1-phthalazone derivative have higher activities in the same pharmaceutical effects than the compound disclosed in the former application. Subsequent investigations on the metabolic passages in animals and clinical tests of 7-alkoxycarbonyl-4-hydroxymethyl-1-phthalazone revealed that when administered to animals and human, the compound is metabolized rapidly to the corresponding 7-carboxy compound. The metabolic hydrolysis leads to the bioinactivation of the alkoxycarbonyl compound, with the result that the duration time of the biological action of the compound is relatively short.

It has now been found that the compounds of the present invention are resistant to metabolic degradation and have prolonged biological activities, compared with the compounds of the prior art. In the test for experimental atherosclerosis induced by cholesterol feeding, the compounds of the present invention were found to be highly active in preventing atherosclerosis and in inhibiting cholesterol deposition on the arterial wall; its potency is roughly three to five times larger than that of the prior art. The present compounds also prevent the enhancement of coagulability and thromogenicity of the blood induced by cholesterol or adrenaline; the potency is also roughly five to ten times larger than that of the prior art. That is, the present compounds prevent more effectively the shortening of clotting time of the blood as well as the enhancement of adenosine diphosphate-induced platelet aggregation in humans.

Furthermore, the present compounds were found to be active to lower and normalize elevated blood pressure in a test for hypertension of spontaneously hypertensive rats, while the compounds of the prior art had no significant activity regarding the elevated blood pressure of the rats. This activity of the present compounds may be related to their inhibitory effect on cyclic AMP phosphodiesterase, which is exemplified in Biological Tests. which follow.

The compounds of the present invention are thus useful for treating hypertensive diseases, atherosclerotic and thrombotic diseases. Such thrombotic diseases include, for example, cerebral thrombosis, coronary thrombosis and peripheral thrombosis. The atherosclerotic diseases include cerebral atherosclerosis, coronary atherosclerosis, arteriosclerosis obliteraus, thromboangitis obliterans, thrombophlebitis, angiopathy of diabetes mellitus, and rephropathy of diabetes mellitus.

The preparation of some starting compounds of the present invention is illustrated hereinafter. The Arabian numerals in the following paragraph correspond respectively to the numbers of the compounds depicted in the reaction scheme which follows it.

The Diels-Adler adduct of ethyl isodehydroacetate and dimethyl acetylenedicarboxylate (1) [of. Berichte der Deutschen Chemischen Gesellschaft, 70, 1354 (1937)] is hydrolysed to the phthalic acid (2). Treatment of (2) with acetic anhydride yields the phthalic anhydride (3). Treatment of the latter with malonic acid in pyridine (80°– 85°C) gives 3-hydroxy-3-methylphthalide (4) in 60% yield. Oxidation of (4) in alkaline water solution with potassium permanganate and subsequent treatment of the solution with hydrazine affords the acid (5) which in turn is esterified to the ester (6) with an 80% overall yield.

methyl-substituted or ethyl-substituted methylene, can be advantgeously prepared as exemplified by the following reaction scheme. 6,8-Dimethyl-4,7-diethoxycarbonyl-1-phthalazone (6) is brominated with N-

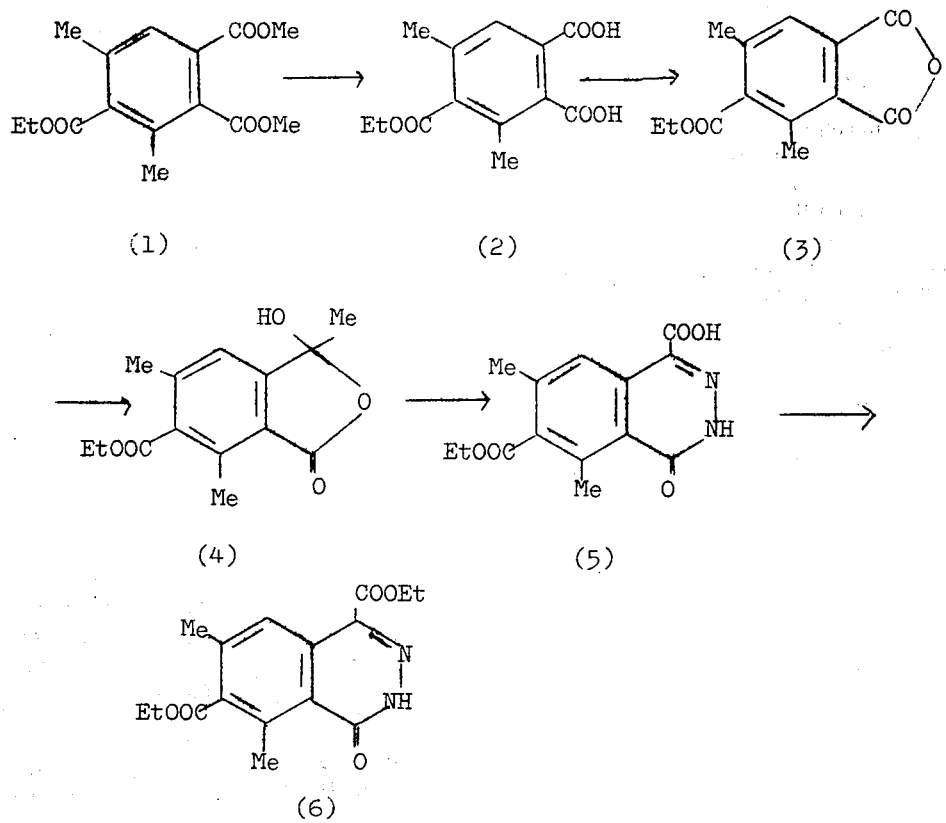

Alternatively, the starting compounds represented by formula (II), wherein $R_3$ joins $R_2$ to form a methylene, bromosuccinimide. Pyrolysis of the monobromo compound (7) affords the lactone (8) in good yield.

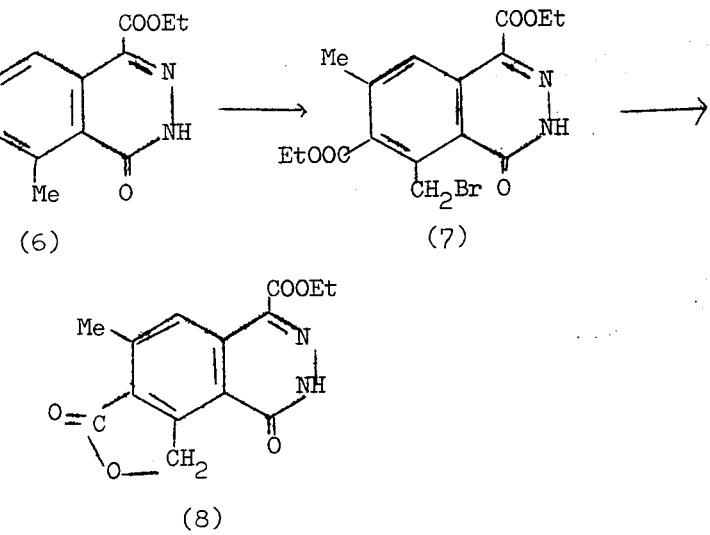

The compounds of formula (II) wherein Z is a group represented by the formula;

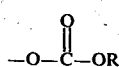

wherein R is as defined above, can be prepared by a known method, for example, by reacting the corresponding carboxylic acid with an alkyl chloroformate such as methyl chloroformate or ethyl chloroformate in the presence of solvent and a dehydrochlorinating agent such as triethylamine. The resulting mixed acid anhydride can be advantageously submitted to the reduction of the present invention without isolation and purification.

A starting compound represented by formula (III) can be prepared, for example, by the following reaction scheme. The Diels-Adler adduct (1) is partially hydrolysed with a slight excess of potassium hydroxide to the mono acid (9). Treatment of the latter with thionyl chloride, and subsequent treatment of the resulting acid chloride with diazomethane affords the diazoketone (10). Treatment of the latter with dilute sulfuric acid affords the isochroman-1,4-dione (11).

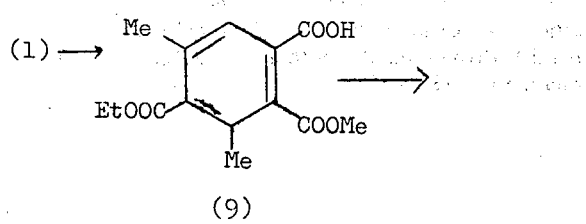

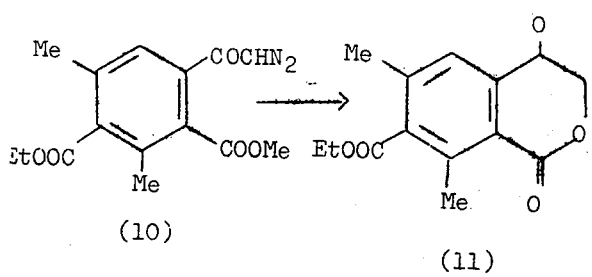

In an embodiment of the process (a) of the invention, a compound of formula (II) is reacted with an alkali metal borohydride in the presence of solvent. A preferred metal borohydride is sodium borohydride used in an equimolecular amount or in an excess, preferably 1.5 – 5 moles per mole of the compound of formula (II). The reaction is preferably carried out in the presence of a metal halide such as calcium chloride, magnesium bromide, lithium bromide or lithium iodide. Solvent, catalyst and temperature, which are used advantageously in the present process, and average yields of the process are tabulated below.

| Z | Solvent | Metal halide | Temp. (C°) | Yield(%) |
|---|---|---|---|---|
| alkoxy | ethanol methanol | CaCl$_2$ | −10° − 30° | 90–95 |
| halogen | dioxane tetrahydrofuran | — | 10° − 100° | 50–80 |
| −O−C(=O)−OR | tetrahydrofuran dioxane | — | −10° − 50° | 50–80 |

In an embodiment of the process (b), a compound of formula (III) is reacted with an equimolecular or excess amount of hydrazine, preferably in the presence of a solvent or diluent. Water and ethanol are advantageous for the solvent or diluent. The reaction is preferably carried out at a temperature between 30° and 100°C.

Alternatively, the compounds of formula (I) wherein R$_3$ is alkyl other than ethyl, can be advantageously prepared, starting from 6,8-dialkyl-7-ethoxycarbonyl-4-hydroxymethyl-1-phthalazone which has been prepared by the above process. For example, treatment of 6,8-dimethyl-7-ethoxycarbonyl-4-hydroxymethyl-1-phthalazone (12) with trifluoroacetic acid or potassium hydroxide affords 6,8-dimethyl-7-carboxy-4-hydroxymethyl-1-phthalazone (13) in good yield, and the latter can be esterified to (14) in an 80% yield with diazoalkane or with N,N-dimethylformamide di-acetal represented by the formula: (CH$_3$)$_2$NCH(OR$_3$)$_2$ wherein R$_3$ is alkyl as defined above, by the method described in Journal of Organic Chemistry, 30, 925(1965), Angewandte Chemie Intern. Ed. Engl., 2, 212 (1963) or Helvetica Chemica Acta, 48, 1746 (1965).

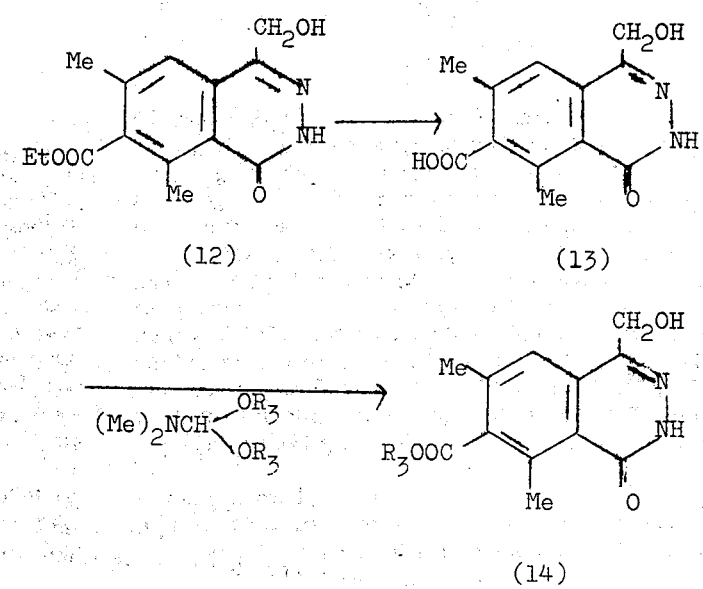

While the preparation for some compounds of the invention is reported later on in detail by means of the examples, we mention the following further compounds falling within the scope of the present application, which may be prepared according to the method herein described.

6,8-diethyl-7-ethoxycarbonyl-4-hydroxymethyl-1-phthalazone
6,8-dimethyl-7-propoxycarbonyl-4-hydroxymethyl-1-phthalazone
6,8-dimethyl-7-n-butoxycarbonyl-4-hydroxymethyl-1-phthalzone
6,8-dimethyl-7-sec-butoxycarbonyl-4-hydroxymethyl-1-phthalazone
6,8-dimethyl-7-iso-butoxycarbonyl-4-hydroxymethyl-1-phthalazone
6,8-dimethyl-7-tert-butoxycarbonyl-4-hydroxymethyl-1-phthalazone
6,8-dimethyl-7-n-amyloxycarbonyl-4-hydroxymethyl-1-phthalazone
6,8-dimethyl-7-isoamyloxycarbonyl-4-hydroxymethyl-1-phthalazone
6,8-dimethyl-7-sec-amyloxycarbonyl-4-hydroxymethyl-1-phthalazone
6,8-diethyl-7-methoxycarbonyl-4-hydroxymethyl-1-phthalazone
6,8-diethyl-7-n-propoxycarbonyl - 4-hydroxymethyl-1-phthazone
6,8-diethyl-7-n-butoxycarbonyl-4-hydroxymethyl-1-phthalazone The compounds of the following formulae:

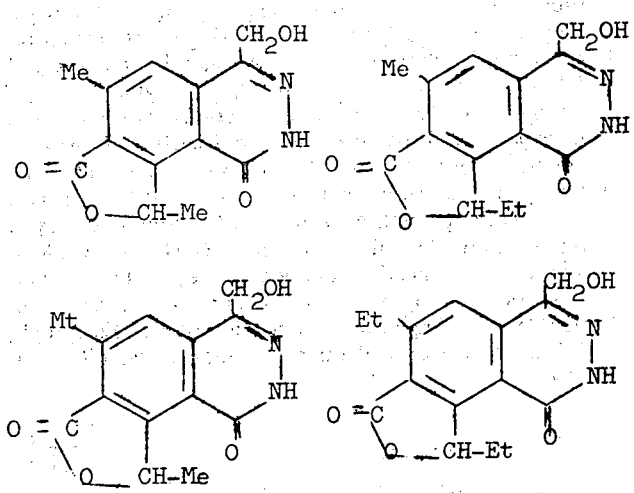

The compounds of the present invention may be administered alone or incorporated into pharmaceutical compositions such as powders, tablets, granules, capsules, troches, suspensions and other dosage forms for oral administration, and solutions, suspensions and other dosage forms for parenteral administration. The effective amount of the compound of formula (I) can be freely changed according to the particular dose intended, but usually is about from 0.1 to 80% based on the combined amount of the carrier or diluent and the compound of formula (I). In short, it may be any desired concentration required for administration at doses ranging from 1 to 100 mg/Kg body weight per day.

The carrier or diluent may be a pharmaceutically acceptable liquid or solid, and the term carrier is also used in this invention to denote adjuvants. Examples of the liquid carrier are distilled water for injection, isotonic sodium chloride solution, Ringer's solution, Locke's solution, polyethylene glycol, ethyl alcohol, propylene glycol, glycerol, and vegetable oil. The solid carrier includes, for example, sodium chloride, glucose, lactose, starch sucrose, cetyl alcohol, cacao butter and spermaceti.

The following examples illustrate the invention, but do not limit the scope of the invention.

EXAMPLE 1

1. Preparation of 5,7-dimethyl-6-ethoxycarbonyl-3-hydroxy-3-methylphthalide

A mixture consisting of 4, 6-dimethyl-5-ethoxycarbonylbenzene-1,2-dicarboxylic acid anhydride (7.8 g. mp. 80°–81°C.), malonic acid (6.5g) dried by heating at 100°C. for 10 hr, and absolute pyridine (7 ml) was heated at 80° – 85°C. for 15 hr. After cooling, 10% aqueous hydrochloric acid was added, and the mixture was extracted with chloroform. The organic layer was washed with water, and extracted with saturated aqueous sodium bicarbonate solution. The sodium bicarbonate extract was made acidic with dilute hydrochloric acid, and further extracted with ethyl acetate. The extract was dried over $MgSO_4$, and the solvent was removed. The resulting residue was recrystallized from ether ~ n-hexane to yield 5,7-dimethyl-6-ethoxycarbonyl-3-hydroxy-3-methylphthalide (5.4g, yield 62%) melting at 118° – 120°C.

2. Preparation of 6,8-dimethyl-4,7-diethoxycarbonyl-1-phthalazone

To a solution of 5,7-dimethyl-6-ethoxycarbonyl-3-hydroxy-3-methylphthalide (1.32g) and potassium hydroxide (1g) in water (100 ml), was added dropwise a solution of $KMnO_4$ (1.58g) in water (80 ml), with stirring. After stirring for an additional 1.5 hr, the precipitated manganese dioxide was filtered, and the filtrate was saturated with carbon dioxide. To the solution was added 80% hydrazine hydrate (5 ml), and then the solution was heated at 70° – 80°C. for 2 hr. After cooling, the solution was acidified wth dilute hydrochloric acid, and the resulting precipitate was filtered and recrystallized from methanol to yield 6,8-dimethyl-7-ethoxycarbonyl-1-phthalazone-4-carboxylic acid (1.1g) melting at 216°–218°C.

6,8-Dimethyl-7-ethoxycarbonyl-1-phthalazone-4-carboxylic acid was refluxed with absolute ethanol and concentrated sulfuric acid, and working up the mixture in an usual manner afforded 6,8-dimethyl-4,7-diethoxycarbonyl-1-phthalazone melting at 159° – 161°C. in a 90 – 95% yield.

3. Preparation of 6,8-dimethyl-7-ethoxycarbonyl-4-hydroxymethyl-1-phthalazone To a stirred solution of sodium borohydride (500 mg) in ethanol (200 ml), were added aliquots of 6,8-dimethyl-4,7-diethoxycarbonyl-1-phthalazone (1.4g) at −5° – 0°C., and then a solution of anhydrous calcium chloride (700 mg) in ethanol (200 ml) was added dropwise to the stirred solution. Stirring continued for an additional 3 hr at the same temperature, and the reaction mixture was allowed to stand overnight at room temperature. The mixture was concentrated under reduced pressure and diluted with water, and its pH value was adjusted to 5 with acetic acid. The resulting precipitate was filtered and recrystallized from ethanol-water to yield 6,8-dimethyl-7-ethoxycarbonyl-4-hydroxymethyl-1-phthalazone (1.2g) melting at 171°–172°C., its spectra are shown below.

UV spectrum: (EtOH) m$\mu$; 218 ($\epsilon$=57000),259 ($\epsilon$=15000), 292 ($\epsilon$=11800), 307 ($\epsilon$=9600), 321 ($\epsilon$=7400)

IR spectrum: (KBr) cm$^{-1}$; 3400 (broad), 2920, 1730, 1650, 1600, 1450, 1280, 1250, 1150, 1120, 1030(broad), 900

NMR spectrum: (measured in dimethyl sulfoxide-d$_6$) $\delta$; 1.25 (t,3H), 2.4 (s, 3H), 2.69 (s, 3H), 4.25 (q, 2H), 4.7(d. 2H), 5.2(t. 1 H), 7.55 (s, 1H)

Anal. Calcd for $C_{14}H_{16}O_4N_2$: C, 60.86; H, 5.84; N, 10.14 Found: C, 60.78; H, 5.80,; N, 10.34

EXAMPLE 2

In an analogous reaction sequence with Example 1. starting from the Diels-Adler adduct of methyl isodehydroacetate and dimethyl acetylenedicarboxylate, the following intermediates and 6,8-dimethyl-7-methoxycarbonyl-4-hydroxymethyl-1-phthalazone were prepared.

i 4,6-dimethyl-5-methoxycarbonylbenzene-1,2-dicarboxylic acid anhydride: mp. 129°–131°C. (recrystallized from ethyl acetate~n-hexane)

ii 5,7-dimethyl-6-methoxycarbonyl-3-hydroxy-3methylphthalide; mp. 104° – 106°C. (recrystallized from ethyl acetate~n-hexane)

iii 6,8-dimethyl-7-methoxycarbonyl-4-carboxy-1-phthalazone: mp. 221° – 223°C. (recrystallized from methanol)

iv 6,8-dimethyl-4,7-dimethoxycarbonyl-1-phthalazone: mp. 240° – 241°C. (recrystallized from methanol)

v 6,8-dimethyl-4-hydroxymethyl-7-methoxycarbonyl-1-phthalazone: mp. 204°–205°C. (recrystallized from methanol), NMR spectrum: (measured in dimethyl sulfoxide-d$_6$) $\delta$ ; 2.4(s, 3H), 2.7(s, 3H), 3.95(s, 3H), 4.6(d, 2H), 5.3(broad, 1H), 7.8(s, 1H)

EXAMPLE 3

Preparation of 6,8-dimethyl-7-ethoxycarbonylisochroman-1,4-dione 3,5-dimethyl-4,6-diethoxycarbonylbenzoic acid was refluxed gently with thionyl chloride, and excess thionyl chloride was distilled off. The resulting residue was treated with an etheral solution of excess diazomethane to yield 3,5-dimethyl-4,6-diethoxycarbonyl-$\omega$-diazoacetophenone (mp. 78°–89°C.) in a 60% overall yield. The latter compound was added to a stirred mixture consisting of 15% aqueous solution of sulfuric acid (2 ml) and dioxane (10 ml) at room temperature. The solution stirred for 2 hr, and then the temperature of the solution was raised to 80° – 90°C. and maintained for 1 hr. The solution was cooled, diluted with water, and extracted with ethyl acetate. The extract was evaporated, and the residue was recrystallized from ethanol to afford 6,8-dimethyl-7-ethoxycarbonyl-isochroman-1,4-dione melting at 142°–144°C. in 73% yield.

Preparation of 6,8-dimethyl-7-ethoxycarbonyl-4-hydroxymethyl-1-phthalazone

A solution consisting of the above isochroman derivative (2 g), 80% hydrazine hydrate (4 ml), and ethanol (50 ml) was refluxed for 2 hr. The solution was concentrated under reduced pressure, diluted with water, and made slightly acidic with dilute hydrochloric acid. The resulting precipitate was filtered and recrystallized from ethanolwater to yield 6,8-dimethyl-7-ethoxycarbonyl-4-hydroxymethyl-1-phthalazone (1.2 g) melting at 171°–172°C., its IR spectrum was identical with that of the sample obtained in Example 1, 3).

EXAMPLE 4

The compound of formula (I), wherein $R_1$ is methyl, and $R_3$ forms together with $R_2$ a methylene group was prepared by the following reaction sequence.

A solution of 6,8-dimethyl-4,7-diethoxycarbonyl-1-phthalazone (3.2g), N-bromosuccinimide (1.9 g) and benzoyl peroxide (100 mg) in carbon tetrachloride (200 ml) was refluxed for 2 hr. After evaporating the solvent, the resulting residue was extracted with ethyl acetate. The extract was washed with water, and the solvent was removed. The residue was recrystallized from ethyl acetate to yield 8-bromomethyl-4,7-diethoxycarbonyl-6-methyl-1-phthalazone (2.86 g) melting at 185° – 190°C.

The bromo compound (1.2 g) above described was heated under vacuum at 185°–190°C. for forty minutes in an oil bath. The resulting solid mass was recrystallized from acetone to afford the compound of the following structure (8) in quantitative yield. It did not melt at 300°C.

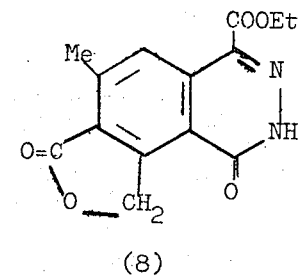

(8)

To a stirred solution of sodium borohydride (45 mg) in ethanol (60 ml), were added aliquots of 112 mg of the compound of (8) above described at −5°–0°C., and then a solution of anhydrous calcium chloride (50 mg) in ethanol (40 ml) was added dropwise to the above solution. The resulting solution was stirred for an additional 3 hr at room temperature and then concentrated under reduced pressure to a volume of about 20 ml. The concentrate was diluted with water, and after adjusting its pH value to 4 – 5 with dilute hydrochloric acid, extracted with ethyl acetate. The solvent was removed from the extract, and the residue was recrystallized from acetone to afford 78 mg of the compound of the following structure (12).

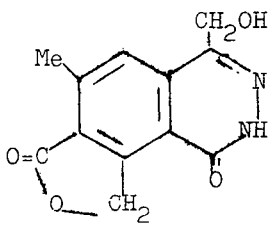

(12)

Its physical properties are shown below.
mp.: did not melt at 300°C.
IR spectrum: (KBr) cm$^{-1}$; 3400 (broad), 1760, 1640, 1610, 1355,
NMR spectrum: (measured in dimethyl sulfoxide-d$_6$); 2.75(s, 3H), 4.7 (s, 2H), 5.45 (broad, 1H), 5.7 (s, 2H), 8.05 (s. 1H), 12.9 (s, 1H),
Mass spectrum: 246 (M$_+$)

EXAMPLE 5

6,8-dimethyl-7-ethoxycarbonyl-4-hydroxymethyl-1-phthalazone (2 g) and trifluoroacetic acid (30 ml) were refluxed for 5 hr. The acid was removed, and the residue was shaken with a mixture of ethyl acetate and 10% aqueous KOH solution. The aqueous layer was separated and made acidic with acetic acid, and the resulting precipitate was filtered and recrystallized from methanol to yield 6,8-dimethyl-7-carboxy-4-hydroxymethyl-1-phthalazone (1.64g) melting at 282°–284°C.
Mass spectrum: 248(M+), 231, 219, 204, 175,
IR spectrum: (KBr) cm$^{-1}$; 3400, 3250, 1705, 1640, 1380, 1280, 1160, 1020, 780, A suspension of 6,8-dimethyl-7-carboxy-4-hydroxymethyl-1-phthalazone in ether was treated with an etheral solution of diazomethane. After decomposing the excess diazomethane, the solvent was removed, and the residue was recrystallized from methanol to yield 6,8-dimethyl-7-methoxycarbonyl-4-hydroxymethyl-1-phthalazone melting at 204°–205°C. Its IR spectrum was identical with that of the sample obtained in Example 2.

A suspension of 6,8-dimethyl-7-carboxy-4-hydroxymethyl-1-phthalazone (430 mg), dimethylformamide di-isopropyl acetal (20 ml) and toluene (80 ml) was refluxed for 26 hr, and then the solvent was removed under reduced pressure. The residue was agitated with a mixture of ethyl acetate and 10% aqueous potassium carbonate solution. The organic layer separated was dried over anhydrous magnesium sulfate and evaporated. The resulting residue was chromatographed on a column of silica gel with chloroform as eluent. From the eluates there was obtained 6,8-dimethyl-7-isopropoxycarbonyl-4-hydroxymethyl-1-phthalazone (185 mg) melting at 176° – 178°C.
IR spectrum: (kBr)cm$^{-1}$; 3400 (broad), 1730, 1640, 1605, 1285, 1240, 1160, 1115,
Mass spectrum: m/e; 290(m$^+$), 248, 247, 232, 231, 204, 202, 200,

BIOLOGICAL TESTS

1. Effect of the present compounds in preventing human platelet aggregation in vitro The compounds of the present invention showed a profound effect in preventing human platlet aggregation induced by ADP (adenosine diphosphate) or adrenaline in vitro.

Samples of human CPRP (citrated platelet-rich plasma) were incubated at 37°C. for 200 sec. with 1/10 volume of saline containing various amount of the compound to be tested. To the mixture was then added ADP (3μMole) or adrenaline (1 μg/ml). Intensity of primary and secondary aggregation was measured with a platelet aggregation meter (Chrono-Log, Model 300).

Intensity of ADP- or adrenaline-induced aggregation of each sample, which was incubated with the compound, was compared with that of the same sample incubated with saline. The ratio was expressed as a percentage of intensity of aggregation with the compound against one with saline. The results are shown in the following Table I.

The intensity of primary and secondary aggregation of platelets was measured by the procedure described in H. Yamazaki, T. Sano, et al.; title[Platelet Functions in Thromboembolic Disorders] *Thrombosis et Diatheses Haemorrhagica* "in press" and the references cited therein.

As shown in Table I, the present compound inhibited the primary aggregation induced by ADP or adrenaline with approximately comparable activity to 4-hydroxymethyl-1-phthalazone (the compound of U.S. Pat. No. 3,840,662) and 7-ethoxycarbonyl-4-hydroxymethyl-1-phthalazone (the compound of U.S. Pat. No. 3,864,343). However, the compound of the present invention inhibited far more effectively the secondary aggregation, compared with the former compounds. That is, the present compounds inhibited the secondary aggregation induced by ADP or adrenaline in a concentration of 1 – 2.5μg/ml with a statistical significance, while 7-ethoxycarbonyl-4-hydroxymethyl-1-phthalazone inhibited the secondary aggregation in a concentration of 5 – 10μg/ml.

Table I

| Incubated with | μg/ml | Cases | ADP 3 μM Primary | ADP 3 μM Secondary | Cases | Adrenaline 1μg/ml Primary | Adrenaline 1μg/ml Secondary |
|---|---|---|---|---|---|---|---|
| Acetylsalicylic acid | 300 | 10 | 108.9±3.6 | 75.5±5.9** | 10 | 107.5±2.6 | 62.7±10.7** |
| (control) | 80 | 10 | 95.7±1.8 | 70.2±10.1* | 10 | 95.6±5.2 | 46.5±7.9** |
|  | 40 | 10 | 98.9±3.4 | 78.0±9.9* | 10 | 105.7±3.3 | 45.0±7.8** |
| 4-hydroxymethyl- | 300 | 10 | 84.5±2.0* | 68.3±3.8* | 10 | 85.4±3.1* | 60.2±8.0* |
| 1-phthalazone | 80 | 10 | 82.4±3.2 | 64.9±6.7 | 10 | 92.3±6.0 | 69.2±7.2 |
| (control) | 40 | 10 | 86.2±2.5 | 72.0±6.8 | 10 | 98.8±5.9 | 85.9±10.1 |
| 7-ethoxycarbonyl- | 80 | 10 | 62.9±5.0** | 15.7±0.4** | 10 | 81.9±6.5* | 33.0±7.1** |
| 4-hydroxymethyl- | 20 | 14 | 77.0±5.1** | 58.6±7.6** | 10 | 92.9±16.9 | 71.7±13.5* |
| 1-phthalazone | 10 | 14 | 81.9±5.2** | 67.1±6.3** | 10 | 97.0±4.1 | 82.1±9.5 |

Table I-continued

| Incubated with | μg/ml | Inhibition Ratio against Human Platelet Aggregation in vitro ||||||
| | | ADP 3 μM ||| Adrenaline 1μg/ml |||
| | | Cases | Primary | Secondary | Cases | Primary | Secondary |
| --- | --- | --- | --- | --- | --- | --- | --- |
| (control) | 5 | 14 | 90.5±5.6 | 84.9±6.3* | 10 | 105.8±6.9 | 80.8±13.9 |
| 6,8-dimethyl-7- | 40 | 10 | 68.5±5.2 | 41.9±2.2 | — | — | — |
| ethoxy-carbonyl-4- | 20 | 10 | 93.1±8.2 | 56.2±6.3** | 10 | 97.5±7.5 | 99.6±13.2 |
| hydroxymethyl-1- | 10 | 10 | 90.6±3.8 | 49.9±6.9** | 10 | 89.1±7.3 | 57.1±16.0** |
| phthalazone | 5 | 12 | 93.3±8.9 | 59.8±11.3** | 10 | 82.4±3.0 | 52.4±7.3 |
| (the present invention) | 2.5 | 10 | 91.7±8.3 | 96.0±8.7 | 10 | 88.5±3.1** | 52.8±7.5** |

*B<0.05   **P<0.01

$$\text{Inhibition ratio} = \frac{\text{Intensity of Aggregation of CPRP incubated with compound}}{\text{Intensity of Aggregation of CPRP incubated with saline}}$$

2. Effect of the present compounds for the prevention and the regression of experimentally induced atherosclerosis The compounds of the present invention showed a definite effect in preventing cholesterol-induced atherosclerosis of experimental animals, and at the same time, they showed also a regression effect against pre-established cholesterol-induced atherosclerosis, diminishing chlesterol contents in the aortic wall of animals.

Forty healthy albino rabbits of the same age and of the same family were used in the experiment. They were divided equally into 5 groups, and to each of the 5 groups were administered orally 4-hydroxymethyl-1-phthalazone (control), 7-ethoxycarbonyl-4-hydroxymethyl-1-phthalazone (control), 6,8-dimethyl-7-ethoxycarbonyl-4-hydroxymethyl-1-phthalazone, and placebo (potato starch) respectively in a daily dose of 1 mg/Kg under 150 g/day of diet containing of 1% cholesterol for 15 weeks.

After the completion of the regimen, the rabbits were killed and the percentage of the surface covered by fatty streaks was measured in each aorta of the rabbits stained with Sundan IV. The percent of the surface covered by fatty streaks in the aorta of the rabbits was measured by the procedure described in T. Shimamoto, F. Numano, T. Fujita; American Heart Journal, 71, 2216 (1966).

The results of the experiment are shown in Table II.

Table II

| Group administered with | Percent of surface covered by fatty streaks (%) |
| --- | --- |
| placebo control (potato starch) | 54.6±5.4 |
| 4-hydroxymethyl-1-phthalazone (control) | 36.8±5.2* |
| 7-ethoxycarbonyl-4-hydroxymethyl-1-phthalazone (control) | 28.8±3.6** |
| 6,8-dimethyl-7-ethoxy-carbonyl-4-hydroxymethyl-1-phthalazone (the present invention) | 16.2±4.3** |

**P<0.01 administered group
*P<0.05 vs placebo control group

For the regressive test, 50 healthy albino rabbits were fed with a diet containing 1% cholesterol for 15 weeks. Five rabbits were killed at the 15th week of the cholesterol feeding and the remaining 45 rabbits were divided into 3 groups. To each of the groups were administered orally 7-ethoxycarbonyl-4-hydroxymethyl-1-phthalazone (control), 6,8-dimethyl-7-ethoxycarbonyl-4-hydroxymethyl-1-phthalazone, and placebo (potato starch), respectively in a daily dose of 1 mg/Kg under 150 g of commercial diet. Five each of the rabbits of the 3 groups were killed after 6, 10 and 20 weeks, respectively. The total contents of cholesterol in the aortic wall were estimated by gas chromatography, the results of which are shown in the Table III.

Table III

| Group administered with | Period (week) | Cholesterol content (μg) |
| --- | --- | --- |
| Placebo control (potato starch) | 6 | 32.1±3.6 |
| | 10 | 33.8±3.0 |
| | 20 | 29.5±5.4 |
| 7-ethoxycarbonyl-4-hydroxymethyl-1-phthalazone (control) | 6 | 24.6±3.0 |
| | 10 | 12.2±3.5 |
| | 20 | 6.4±2.7 |
| 6,8-dimethyl-7-ethoxycarbonyl-4-hydroxy-methyl-1-phthalazone (the present compound) | 6 | 20.8±3.1 |
| | 10 | 9.7±4.2 |
| | 20 | 4.2±1.8 |

1. The total content of cholesterol in the aortic wall was measured by the procedure described in T. Shimamoto, F. Numano, T. Fujita et al.; Asian med. Journal, 8. 12 (1965) 2. The total cholesterol content at the end of the first 15 weeks was 42.5 ± 8.5 μg/mg dry weight. 3. The total chloesterol contents indicated in Table III were shown in μg per one mg of the dried aortic wall. The value in the Table is the average figure for 5 rabbits 3. Effect of the present compounds in inhibiting cyclic AMP phosphodiesterase in rabbits aortic wall and human platelet The compounds of the present invention showed a definite inhibitory effect against cyclic AMP phosphodiesterase in rabbits aortic walls and human platelets A supernatant of homogenized intima, media of the aortic wall of rabbits, or human platelet-rich plasma, was incubated with the reagent mixture consisting of tritum-labeled cyclic AMP (adenosine-3', 5'-cyclic monophosphate) and various amounts of the compound.

The incubated mixture was purified by column chromatography, and the fraction containing nucleotides was quantitatively analyzed with a liquid scintillation counter.

Table IV shows the inhibitory effect of these compounds against cyclic AMP phosphodiesterase. The figures in the table show the amount of the compound required to produce 50% inhibition of cyclic AMP phosphodiesterase.

As shown in Table IV, the present compound is more highly active to inhibit diphosphoesterase than theophylline, caffeine or compounds of the prior art. It means that the present compounds are effective in increasing the concentration of cyclic AMP in platelets and in the aortic wall.

Table IV

| Compound | | Platelet (human) | I₅₀(μMole) Aortic Wall Intima (rabbit) | Media (rabbit) |
|---|---|---|---|---|
| 7-ethoxycarbonyl-4-hydroxymethyl-1-phthalazone | (control) | 57 | 52 | 144 |
| theophylline | (control) | 91 | 127 | 155 |
| caffeine | (control) | 350 | — | 460 |
| 6,8-dimethyl-7-ethoxycarbonyl-4-hydroxymethyl-1-phthalazone | (the present compound) | 4.1 | 1.6 | 24 |

The procedure of the experiment was carried out in accordance with the method described in H. Hidaka and M. Shibuya: title "A new assay of cyclic nucleotide phosphodiesterase and its application to humans", *Biochemical Medicine*, (in press).

4. Hypotensive effect of the present compounds in spontaneous hypertensive rats

The present compounds have a unique hypotensive effect in spontaneously hypertensive rats. The spontaneously hypertensive rats, abbreviated as SH rats, are produced by selective breeding of spontaneously hypertensive rats and continuous inbreeding with hypertensive mates, and they might be acknowledged as genetically hypertensive. It is believed that SH rats have a striking similarity to human essential hypertension and their reactions can be extrapolated to this morbid condition.

4-Hydroxymethyl-1-phthalazone and 7-ethoxycarbonyl-4-hydroxymethyl-1-phthalazone disclosed in the prior art did not exhibit a significant hypotensive effect in intraperitoneal or oral doses up to 50 mg/Kg. On the other hand, the present compounds exhibited a striking hypotensive effect in doses of 0.78 to 50 mg/Kg given intraperitoneally or orally as shown in Table V-b.

In the blood pressure test, SH rats weighing 210 – 250 g and aged 13–15 weeks were used, and the compounds tested were administered intraperitoneally. Each value in the Table V hows an average figure for three rats.

Table V-a

| Compound (Dose: 50 mg/Kg) | | Before | Blood Pressure (time hrs.) 1 | 3 | 6 | 24 | 48 |
|---|---|---|---|---|---|---|---|
| 4-hydroxymethyl-1-phthalazone | Blood Pressure | 183 | 178 | 179 | 180 | 182 | 184 |
| 7-ethoxycarbonyl-4-hydroxymethyl-1-phthalazone | Blood Pressure | 178 | 165 | 176 | 180 | 179 | 184 |

Table V-b

Compound: 6,8-dimethyl-7-ethoxycarbonyl-4-hydroxmethyl-1-phthalazone

| Dose mg/Kg | | Before | Blood Pressure & Depression % Time (hr) after Dosing 1 | 3 | 6 | 24 | 48 |
|---|---|---|---|---|---|---|---|
| 50 | Blood Pressure | 170 | 165 | 132 | 110 | 145 | 152 |
|  | Depresion % |  | 2.9 | 22.4 | 35.3 | 14.7 | 10.6 |
| 12.5 | Blood Pressure | 175 | 173 | 155 | 120 | 142 | 155 |
|  | Depression % |  | 1.1 | 11.4 | 28.6 | 18.9 | 11.4 |
| 3.1 | Blood Pressure | 173 | 170 | 138 | 110 | 135 | 150 |
|  | Depression % |  | 1.7 | 20.2 | 36.4 | 22.0 | 13.3 |
| 0.78 | Blood Pressure |  |  |  |  |  |  |

5. Toxicity Test

The results of toxicity test ($LD_{50}$) of the compounds of the present invention with the compounds of the prior art are shown in the following table. The test was carried out by oral administration using mice. The toxicity test shows that these compounds are comparably nontoxic.

| | | $LD_{50}$(mg/Kg) |
|---|---|---|
| 4-hydroxymethyl-1-phthalazone | | 4,000 |
| 7-ethoxycarbonyl-4-hydroxymethyl-1-phthalazone | | 5,000 |
| 6,8-dimethyl-7-ethoxycarbonyl-4-hydroxymethyl-1-phthalazone | (the present compound) | 4,250 |

What we claim is:

1. A compound of the formula:

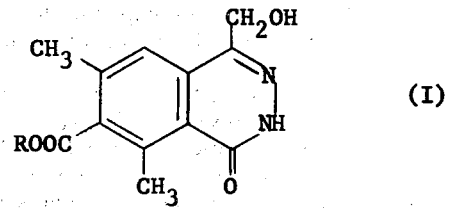

(I)

wherein R is a member selected from the group consisting of alkyl of from 1 to 5 carbon atoms.

2. The compound of claim 1, wherein said compound is 6,8-dimethyl-7-ethoxycarbonyl-4-hydroxymethyl-1-phthalazone.

3. A compound of the formula:

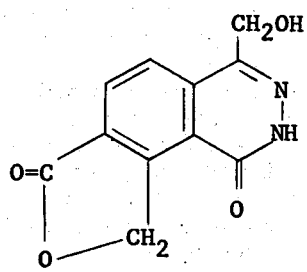

* * * * *